United States Patent [19]

Feitler et al.

[11] Patent Number: 4,883,881
[45] Date of Patent: Nov. 28, 1989

[54] PREPARATION OF UV GRADE SYNTHETIC PYRIDINE

[75] Inventors: David Feitler, New Windsor; Henry Wetstein, Monroe, both of N.Y.

[73] Assignee: Nepera, Inc., Harriman, N.Y.

[21] Appl. No.: 186,825

[22] Filed: Apr. 27, 1988

[51] Int. Cl.$^4$ ................. C07D 213/02; C07D 213/127
[52] U.S. Cl. ...................................... 546/353; 546/250
[58] Field of Search ................ 260/701, 704; 546/250, 546/353

[56] References Cited

U.S. PATENT DOCUMENTS

| | | | |
|---|---|---|---|
| 2,058,435 | 10/1936 | Fisher | 546/353 |
| 2,335,823 | 11/1943 | Cislak et al. | 203/37 |
| 2,363,158 | 11/1944 | Stasse | 203/52 |
| 2,425,220 | 8/1947 | Baney | 203/83 |
| 3,431,266 | 3/1969 | Masciantonio et al. | 546/353 |
| 3,493,473 | 2/1970 | Naito et al. | 203/84 |
| 4,810,798 | 3/1989 | Lendle et al. | 546/353 |

FOREIGN PATENT DOCUMENTS

| | | | |
|---|---|---|---|
| 257257 | 6/1988 | German Democratic Rep. | 546/353 |
| 257258 | 6/1988 | German Democratic Rep. | 546/353 |
| 1397437 | 5/1988 | U.S.S.R. | 546/353 |

OTHER PUBLICATIONS

Perrin, D. D. and Armarego, W. L. F., *Purification of Laboratory Chemicals*, Pergamon Press, New York, N.Y.

Riddick, J. A. and Bunger, W. B. and Sakano, T. K.; "Physical Properties and Methods of Purification—Organic Solvents", *Techniques of Chemistry*; vol. 11, 4th Edition, pp. 1076-1079.

Harmsen, L. W. F., Removal of Nitrogen Compounds From Waste Water; CA vol. 108, No. 06, Sec. 160, Abstract No. 043304.

*Primary Examiner*—Alan L. Rotman
*Attorney, Agent, or Firm*—Millen, White & Zelano

[57] ABSTRACT

A method of preparing UV-grade synthetic pyridine from a pyridine-containing reaction product mixture which also contains at least one other compound which is UV absorbing to a sufficient extent that said pyridine mixture is not UV grade, said mixture being obtained from the condensation reaction, over an effective catalyst, of one or more aldehydes and/or ketones with one or more amines and/or ammonia, comprises recovering from said mixture a pyridine-water azeotrope effective to separate pyridine therefrom sufficiently free of UV-absorbing compounds to be UV grade.

12 Claims, No Drawings

PREPARATION OF UV GRADE SYNTHETIC PYRIDINE

BACKGROUND OF THE INVENTION

This invention relates to a method for preparing UV grade synthetic pyridine from the product mixture resulting from the conventional catalytic condensation reaction of aldehydes and/or ketones and ammonia or amines.

A wide variety of methods has been applied to the problem of purifying pyridine for its various uses. Thus, for example, Perrin et al., *Purification of Laboratory Chemicals*, Pergammon Press (1966), 248–249, describe conventional methods for separating pyridine from homologs. These include crystallization of the oxalates, complex formation with $ZnCl_2$ or $HgCl_2$, fractional crystallization, vapor phase chromatography, etc. Riddick et al., in *Organic Solvents*, 4th Ed., "Techniques of Chemistry", Vol. 2, Ed. A. Weissberger, J. Wiley & Sons, 1986, describe the purification of pyridine and mentioned some of the same techniques for separating pyridine from its homologs. Also mentioned is treatment with cerium sulfate, distillation from potassium hydroxide or barium oxide, treatment with alumina, chromatography, fractional distillation (to prepare pyridine suitable for use in chemical reaction studies), etc.

It is further known that fractional distillation and azeotropic distillation techniques have been utilized in separations involving other aromatic bases for various purposes. Thus, U.S. Pat. No. 3,493,473 removes a variety of impurities from pyridine by azeotropic distillation of impurity-water azeotropes. Impurities include benzene, toluene, xylenes, nitriles, permanganate reducible materials and Ehrlich's reagent positive materials. U.S. Pat. No. 3,431,266 distills from a mixture of pyridine sulfate and sulfuric acid, a pyridine/water mixture exceeding the azeotrope. Subsequently, a pyridine/water azeotrope is freed from the distillate. However, "pyridine" is defined to include homologs such as the picolines, glutidines, quinolines, etc. U.S. Pat. No. 2,363,158 uses a pyridine/water hydrocarbon azeotrope to separate pyridine from piperidine. U.S. Pat. No. 2,058,435, on the other hand, discloses how the pyridine/water azeotrope can disturb efforts to purify pyridine (col. 1, lines 20–25). U.S. Pat. No. 2,425,220 applies azeotropic distillation to the recovery of pyrrole from fractions of heterocyclic nitrogen compounds including picolines and lutidines using a pyrrole/water azeotrope. U.S. Pat. No. 2,335,823 separates 2,6-lutidine, 3-picoline and 4-picoline from a mixture by sequentially distilling the water azeotropes of each of these.

However, none of these references deals with the problem of purifying pyridine to the extent necessary to meet commercial UV grade specifications. The pyridine-containing reaction mixtures which result from conventional synthetic methods for preparing pyridine do not meet UV specifications. But the latter must be met for a variety of commercial uses of pyridine, e.g., as a specialty solvent.

Pyridine is prepared industrially by catalytic condensation of aldehydes and/or ketones with ammonia and/or amines. A wide variety of catalysts, reactants, feed ratios, reaction conditions, is known. See, e.g., U.S. Pat. Nos. 4,675,410, 4,149,002, 3,907,915, 3,946,020 and 2,807,618; "Heterogeneous Conversion of Acylic Compounds to Pyridine Bases—A Review", *Applied Catalysis*, 23, (1986), 1–14; "Pyridine and Pyridine Derivatives", Goe, Gerald L., Kirk-Othmer, 3rd Edition, Vol. 19, John Wiley & Sons, p. 454 (1978); "Synthetic and Natural sources of the Pyridine Ring", Bailey et al., pp. 1–252 in "Heterocyclic Compounds", Volume 14, "Pyridine and Its Derivatives", John Wiley & Sons, New York (1984); and many other references, all of which are entirely incorporated by reference herein. The literature is devoid of any mention of how UV grade pyridine can be recovered from the product of such reactions.

Although it is known that the reaction mixtures fail to meet UV specifications, it is not known which components of such mixtures are responsible for the undesired UV absorption. Because of the high complexity of the impurity spectrum of these mixtures, determination of their compositional details is a difficult problem.

In attempting to remove the unknown UV impurities, many of the previously successful chemical purification methods for pyridine were applied. In all cases, they failed to produce UV grade pyridine. Similarly, conventional fractional distillation also failed to produce UV grade pyridine.

SUMMARY OF THE INVENTION

It has now surprisingly been discovered that the nature of the reaction mixtures resulting from the mentioned condensation reactions is such that recovery of a pyridine/water azeotrope from the mixtures produces pyridine in a form sufficiently free from UV interferants to qualify as UV grade.

Consequently, this invention relates to a method for preparing UV grade synthetic pyridine from a pyridine-containing reaction product mixture which also contains at least one other compound which is UV absorbing to a sufficient extent that said pyridine mixture is not UV grade, said mixture being obtained from the condensation reaction, over an effective catalyst, of one or more aldehydes and/or ketones with one or more amines and/or ammonia, comprising recovering from said mixture a pyridine-water azeotrope effective to separate pyridine therefrom sufficiently free of UV-absorbing compounds to be UV grade.

The product mixtures suitable for use in this invention include all of those which are obtained from the wide variety of prior art catalytic condensations, such as those mentioned above. These include those using amorphous or crystalline zeolite catalysts, fixed or fluid beds, batch or continuous processing, binary, ternary or higher mixtures of aldehydes and/or ketones, etc., i.e., in essence any of the conventional variants described in the references cited above as well as many others.

The types of impurities successfully removable by the process of this invention include but are not limited to aromatics like benzene and toluene, alcohols such as methanol and ethanol, ketones such as acetone, aldehydes such as acetaldehyde and isobutyl aldehyde, imines such as acetaldehyde methylimine, nitriles such as butyronitrile, isobutyronitrile, dimethylamine acetonitrile, pyrrole and alkyl pyrroles such as N-methylpyrrole, pyrimidine and alkylpyrimidines, pyrazine and alkylpyrazines (e.g., N-methyl- and/or 2-methylpyrazine), pyridazine, thiophenes etc. Homologs such as the picolines, especially α-picoline or β-picoline can also be removed by the process of this invention.

Based on studies subsequent to the discovery of this invention, the most prevalent UV interferant successfully removed by this invention appears to be pyrazine or an alkylpyrazine. Other prevalent UV impurities appear to be pyrimidine, pyrrole or alkylpyrrole, pyridazine, nitriles, etc.

This invention is capable of removing any of he usual amounts of UV impurity contents to a degree sufficient to satisfy UV grade specifications. Typically, the impurities will be contained individually in amounts of 1,000–5,000 ppm, more often less than 1,000 ppm, e.g., less than 500 ppm. In the case of pyrazine, 10 ppm are determined sufficient to cause pyridine to fail UV specifications. Using the process of this invention, these interfering amounts of UV absorbers can be lowered to the levels necessary for commercial UV specs to be met. These levels or content ranges are less than 100 ppm, preferably less than 50 ppm, most preferably less than 25 ppm, and especially less than 10 ppm or 5 ppm, e.g., especially into the range of 1–25 or 1–20 ppm, preferably 1–10 or 1–5 ppm, or even lower.

By "UV grade pyridine" is meant pyridine which meets at least one commercial UV grade specification, including the following:

| UV Grade Pyridine Specifications | | | | | | |
|---|---|---|---|---|---|---|
| Source | | | | | | |
| Aldrich | $\lambda$* | 400–350 | 335 | 330 | 315 | |
| (87) | A | 0.01 | 0.05 | 0.15 | 1.0 | |
| Merck | $\lambda$ | 400 | 350 | 340 | 330 | |
| (EM Sciences) | A | 0.01 | 0.1 | 0.3 | 1 | |
| Baker | $\lambda$ | 400–345 | 335 | 325 | 305 | |
| (Catalogue 80) | A | 0.01 | 0.02 | 0.05 | 1.0 | |
| Fluka | $\lambda$ | 360 | 350 | 340 | 330 | 320 | 310 |
| (1986-7) | A | 0.0044 | 0.013 | 0.0315 | 0.076 | 0.14 | 0.35 |
| Riedel | $\lambda$ | 340 | 330 | 310 | 305 | | |
| deHahn | A | 0.0088 | 0.0605 | 0.187 | 0.699 | | |

*all $\lambda$ values in nanometers.

The water pyridine azeotrope which has been employed successfully in conjunction with this invention is that boiling at about 93°–94° C., i.e., at 93.6° C. and having a composition of about 58–59% pyridine and 42–41% water, believed to be more precisely, 58.7% pyridine and 41.3% water.

Based on analyses performed after the discovery of this invention, it is believed that the invention is successful because of the nature of the contaminants now believed to be likely causes of the UV absorption problem and their respective boiling points and/or water-azeotrope boiling points. Thus, for example, pyridine boils at 115.3° and its azeotrope with water (58.7% pyridine/41.3% H₂O) at 93.6°. N-methylpyrrole boils at 112°–113°; pyrazine boils at 114°–115° C. and has a water azeotrope (40% water) which boils at 95.5°; 2-methylpyrazine boils at 133° and has a water azeotrope (55% water) which boils at 97°. Pyrimidine boils at 123°–124°; pyridazine boils at 208°,dimethylaminoacetonitrile boils at 137°–138°; dimethylcyanamide boils at 161°–163°; etc. See *Azeotropic Data III, ACS Advances in Chemistry Series* 116, Lee H. Horsley, American Chemical Society, 1973, for these and other data.

The starting material reaction mixture typically is not that which directly results from the mentioned conventional catalytic condensation reactions. Rather, these direct product mixtures are normally first extracted with benzene in accordance with fully conventional procedures. The non-aqueous benzene extracted phase preferably is employed in conjunction with this invention. These typically will have pyridine contents in the range of 40–75 wt.% and typical benzene contents of 10–40 wt.%, neither of these amounts being at all critical. The benzene can be removed by preliminary treatment or in a low boiling cut in the distillation procedure.

Normally, benzene is removed in a continuous fashion by distillation and a crude pyridine fraction is isolated from the benzene feed stream by either batch or continuous distillation. To this crude pyridine or a purer pyridine sample, sufficient water is added in accordance with conventional considerations to ensure that the desired pyridine-water azeotropic cut can be obtained at the desired yield and purity. Typically, sufficient water is added to provide a pot composition 1 having 0.1–90% by weight water, preferably 3–50% by weight and most preferably 8–20% by weight water. The precise amount of water is also not critical.

Like the water addition step, determination of conventional distillation conditions and parameters will be in accordance with fully conventional considerations given the surprising discovery of this invention that water azeotropic distillation can be successfully employed to prepare UV grade pyridine. Optimum azeotropic fractional distillation configurations can be determined, for example, in accordance with the fully conventional considerations thoroughly discussed in any text dealing with the matter, e.g., *Perry's Chemical Engineer's Handbook*, 6th Edition, McGraw-Hill, Inc. pp. 13-57 to 13-71 (1984). Typical configurations and features include number of plates, reflux ratios, physical dimensions, temperatures, etc. Typically, the distillation of this invention will be carried out under pressures in the range of 0–20 atm, preferably 0.5–5 atm, most preferably 1–3 atm. Typical ranges for the number of plates are generally 1–100, more preferably 2–90, most preferably 10–80, and for reflux ratios, 1–1000, preferably 2–500, most preferably 30–80.

Once the pyridine-water azeotrope has been separated in accordance with this invention, conventional techniques for isolating the pyridine can be employed, e.g., by conventionally breaking the water-pyridine azeotrope by addition of benzene followed by fractional distillation to prepare substantially dry pyridine. Other conventional techniques can be used also, e.g., drying operations, extraction, saltation, redistillation, etc., in accordance with fully conventional considerations, e.g., as discussed in any of a wide variety of relevant texts, e.g., *Chemist's Companion*, Gordon, Arnold J. et al., John Wiley and Sons (1972).

The UV grade pyridine prepared in accordance with this invention can be employed for any of the purposes for which commercially available UV grade pyridine has heretofore been employed, e.g., as a high grade solvent or solvent component for high pressure liquid chromatography (HPLC), or as a solvent or solvent component for use in taking UV spectra of other materials, etc.

A preferred starting material pyridine-containing reaction mixture is that of U.S. Pat. No. 4,675,410.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

A crude pyridine (>95%) or 1 degree pyridine (>98%) prepared by the process of U.S. Pat. No. 4,675,410 (1300 ml) is placed in a distillation apparatus consisting of a 2000 ml roundbottomed three-necked flask, a mirrored, vacuum-jacketed distillation column (4 ft. high, 2.5 cm id) filled with Goodloe 316 stainless steel distillation packing, a takeoff head, and heating mantle. Temperatures are measured using thermometers mounted in one neck of the flask and in the distillation head. Distilled water is added and the apparatus is closed and brought to reflux. As the distillation proceeds, it is stopped periodically to allow the addition of more water. A total of 950 cc of water is added in aliquots during the course of the distillation. A reflux ratio of 50:1 is maintained. An initial 235 cc of aqueous material is discarded. Pyridine-water azeotrope (1580 cc, @93° C.) is collected and shown to be properly transparent in its UV spectrum in accordance with its dilution with water.

Example 2

Pyridine-water azeotrope (1580 cc) produced in the manner described in Example 1 is placed in a roundbottomed flask (5000 ml) fitted with a Dean-Stark takeoff apparatus. Reagent grade benzene (200 cc) is added and the system closed and brought to reflux. Water (710 cc) is recovered. After cooling, the Dean-Stark apparatus is removed and replaced with a vacuum-jacketed, mirrored distillation column, and a fractionating head as in Example 1. Water (30 cc) is added, the system is closed and the mixture brought to reflux at a reflux ratio of 40:1. After the removal of the benzene-water azeotrope (220 cc, @64° C.), a small amount of pyridine water azeotrope (90 cc, @94° C.) is collected. After a small forecut (30 cc, @94°-115° C.), dry, UV transparent pyridine (500 cc, @115° C.) is collected.

| UV pyridine (This Invention) | $\lambda$* | 400 | 340 | 330 | 320 | 310 | 305 |
|---|---|---|---|---|---|---|---|
| | A | — | 0.001 | 0.006 | 0.025 | 0.120 | 0.58 |
| Bottoms after removal of azeotrope per this invention | $\lambda$ | 400 | 340 | 330 | 320 | 310 | 305 |
| | A | 0.279 | 0.834 | 0.981 | 1.182 | 1.562 | 1.774 |

*all $\lambda$ values in nanometers

Example 3

The residue from Example 1 was distilled to give pyridine meeting ACS specifications. The pyridine did not meet UV specifications.

| $\lambda$* | 400 | 340 | 330 | 320 | 310 | 305 |
|---|---|---|---|---|---|---|
| A | 0 | 0.014 | 0.411 | 0.722 | 0.765 | 1.175 |

*all $\lambda$ value in nanometers

This shows that some of the UV impurities boil higher, or have azeotropes boiling higher than the pyridine with azeotrope.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of preparing UV-grade synthetic pyridine from a pyridine-containing reaction product mixture which also contains at least one other compound which is UV absorbing to a sufficient extent that said pyridine mixture is not UV grade, said mixture being obtained from the condensation reaction, over an effective catalyst, of one of more aldehydes and/or ketones with one or more amines and/or ammonia,
comprising recovering from said mixture a pyridine-water azeotrope effective to separate pyridine therefrom sufficiently free of UV-absorbing compounds to be UV grade.

2. A method of claim 1, wherein said recovered pyridine-water azeotrope is broken by adding benzene thereto and distilling the resultant mixture to recover substantially anhydrous pyridine.

3. A method of claim 1, wherein said non-UV grade pyridine mixture is the non-aqueous phase of a benzene extraction of the direct reaction product mixture obtained in said condensation reaction.

4. A method of claim 1, wherein prior to said recovering step, water is added to said non-UV grade pyridine mixture.

5. A method of claim 3, wherein prior to said recovering step, water is added to said non-UV grade pyridine mixture.

6. A method of claim 1, wherein said other compound is at least one of pyrazine or an alkyl pyrazine.

7. A method of claim 1, wherein said pyridine-water azeotrope boils at about 93°-94° C.

8. A method of claim 6, wherein said mixture also comprises pyrimidine, alkylpyrimidine, pyrrole or alkylpyrrole.

9. A method of claim 6, wherein said mixture also comprises pyrimidine.

10. A method of claim 6, wherein the content of the pyrazine compound(s) in the non-UV grade pyridine mixture is about 100-500 ppm and the content of said pyrazine compound(s) in the UV-grade mixture is 1-20 ppm.

11. A method of claim 10, wherein said pyrazine compound content in said UV grade mixture is less than 10 ppm.

12. A method of claim 1, wherein the pyridine-water azeotrope is recovered by a fractional distillation carried out with a reflux ratio of 30-80 and a number of theoretical plates of 10-80.

* * * * *